US00PP36959P3

(12) United States Plant Patent
Juist

(10) Patent No.: US PP36,959 P3
(45) Date of Patent: Sep. 16, 2025

(54) ***LEUCANTHEMUM* PLANT NAMED 'LEUZ0008'**

(50) Latin Name: *Leucanthemum maximum*
Varietal Denomination: LEUZ0008

(71) Applicant: SYNGENTA CROP PROTECTION AG, Basel (CH)

(72) Inventor: Monique Juist, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 18/831,214

(22) Filed: Sep. 20, 2024

(65) Prior Publication Data

US 2025/0024765 P1 Jan. 16, 2025

(51) Int. Cl.
*A01H 6/14* (2018.01)

(52) U.S. Cl.
USPC ..... Plt./263.1
CPC ..... *A01H 6/14* (2018.05)

(58) Field of Classification Search
USPC ..... Plt./263.1
CPC ..... A01H 6/14; A01H 5/02
See application file for complete search history.

(56) References Cited

PUBLICATIONS

CPVO Register—CPVO Application Consultation (Year: 2024).*

* cited by examiner

*Primary Examiner* — Keith O. Robinson
(74) *Attorney, Agent, or Firm* — Dale Skalla

(57) ABSTRACT

A new *Leucanthemum* plant named 'LEUZ0008' particularly distinguished by its floriferousness, early flowering, a white flower color, compact growth habit and big flowers.

1 Drawing Sheet

Latin name of the genus and species of the plant claimed: *Leucanthemum maximum.*

Varietal denomination: 'LEUZ0008'.

BACKGROUND OF THE NEW PLANT

The present invention comprises a new distinct cultivar of *Leucanthemum*, botanically known as *Leucanthemum maximum*. and hereinafter referred to by the variety name 'LEUZ0008'.

The new *Leucanthemum* is a product of a planned breeding program. The new *Leucanthemum* cultivar is floriferous, is early flowering, with white flower color, a compact growth habit and big flowers.

The present cultivar originated from a cross made in 2018 in a controlled environment in Enkhuizen, The Netherlands.

The female parent was a *Leucanthemum* selection identified as 'K4515-3', not patented. Compared to 'LEUZ0008', it has bigger flowers, more flower petals that are more deep incised at the apice.

The male parent was a *Leucanthemum* selection identified as 'PERAT4224-(4).4V', not patented. Compared to 'LEUZ0008', it has smaller flowers and a yellow flower color in young and mature stage.

The resulting seeds were sown in March 2019. 'LEUZ0008' was selected as one flowering plant within the progeny of the stated cross in June 2019 in a controlled environment in Enkhuizen, The Netherlands.

The first act of asexual reproduction of 'LEUZ0008' was accomplished when vegetative stem cuttings were propagated from the initial selection in October 2019 in a controlled environment in Enkhuizen, The Netherlands Horticultural examination of plants grown from cuttings of the plant initiated in March 2020 and continuing thereafter, has demonstrated that the combination of characteristics as herein disclosed for 'LEUZ0008' are firmly fixed and are retained through successive generations of asexual reproduction 'LEUZ0008' has not been observed under all possible environmental conditions. The phenotype may vary significantly with variations in environment such as temperature, light intensity, and day length.

This new *Leucanthemum* plant is a perennial in all climatical zones in the US. Temperature tolerance: Cold tolerance to −20 degrees C. Heat tolerance to 35 degrees C.

The following traits have been repeatedly observed and are determined to be basic characteristics of the new variety. The combination of these characteristics distinguishes this *Leucanthemum* as a new and distinct variety. The new *Leucanthemum* cultivar is floriferous, is early flowering, with white flower color, a compact growth habit and big flowers.

DESCRIPTION OF THE DRAWINGS

This new *Leucanthemum* plant is illustrated by the accompanying photographic drawings which shows blooms, buds and foliage of the plant in full color. The colors showing being as true as can be reasonably obtained by conventional photographic procedures.

The photographic drawings show in FIG. 1 a flowering plant of the new variety and in FIG. 2 a close-up of the flowers.

Figure 1:
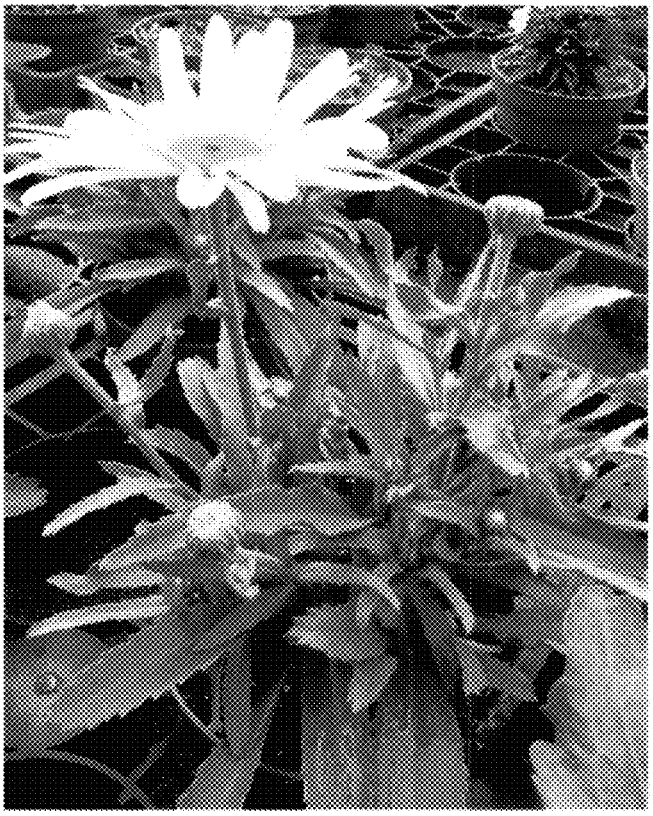
Figure 2:
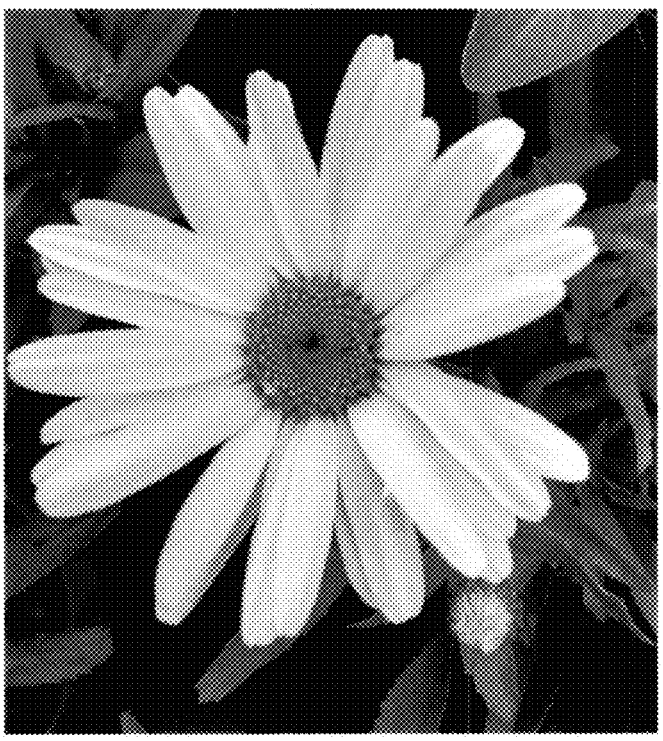

The photographs were taken in June 2024 from plants growing outdoors in 12 cm pots in Enkhuizen, The Netherlands. These plants were approximately 14 weeks of age.

DETAILED BOTANICAL DESCRIPTION

The plant descriptions and measurements were taken in August 2024 in Enkhuizen, The Netherlands on outdoor plants grown in 12 cm pots. These plants were about 22 weeks old.

Color references are made to The Royal Horticultural Society Colour Chart (R.H.S.) 2001.

TABLE 1

DIFFERENCES BETWEEN THE NEW CULTIVAR 'LEUZ0008' AND A SIMILAR CULTIVAR

| | 'LEUZ0008' | 'LEUZ0003' (U.S. Pat. No. PP30826) |
|---|---|---|
| Earliness: | Very early | Medium early |
| Vigor: | Low in vigor | Medium vigorous |
| Width of leaves: | Rather narrow | Wide |

The plant:

Propagation:

*Type cutting.*—Terminal cuttings.

*Time to initiate roots.*—21 days at 20 degrees C.

*Time to produce a rooted cutting.*—6 weeks.

*Root description.*—Fine, fibrous and white in color (RHS 155D).

Plant description:

*General appearance.*—Heavy, sturdy plant with dark leaves (RHS 137A upper surface, RHS 138A lower surface) and big inflorescences.

*Branching habit.*—Basal branching.

*Plant height.*—32 cm including lower, 14-20 cm without flower.

*Plant spread.*—25 cm.

Lateral branch description:

*Length.*—

*Primary.*—14-20 cm.

*Secondary.*—1-12 cm. Secondary shoots developing 1-12 cm from base of primary shoot.

*Diameter.*—0.4 cm.

*Texture.*—Smooth, glabrous.

*Internode length.*—1.5-3 cm.

*Color.*—RHS 137C.

*Number of lateral branches per plant.*—12 generative branches; 7-9 vegetative shoots developing (1-3 cm long).

Foliage description:

*Arrangement.*—Alternate.

*Length, mature leaves.*—13-15 cm.

*Width, mature leaves.*—1.7-2.0 cm.

*Shape.*—Ensiform.

*Apex.*—Acute.

*Base.*—Attenuate.

*Margin.*—Dentate.

*Pubescence.*—

*Upper surface.*—Lightly pubescent.

*Lower surface.*—Lightly pubescent, medium pubescent around veins.

*Texture.*—Smooth, glabrous.

*Color, young foliage, upper surface.*—RHS 137B.

*Color, young foliage, lower surface.*—RHS 137C.

*Fully expanded foliage, upper surface.*—RHS 137A.

*Fully expanded foliage, lower surface.*—RHS 138A.

*Petiole.*—Absent.

*Veins, venation type.*—Pinnate.

*Veins, color upper surface.*—RHS 143C.

*Veins, color lower surface.*—RHS 143C.

Inflorescence:

*Form.*—Actinomorphic.

*Inflorescence position.*—Terminal.

*Disc and ray floret arrangement.*—Acropetally on a capitulum.

*Number of inflorescences per plant.*—20-25.

*Lasting quality.*—40 days.

*Fragrance.*—None.

Bud (described before color developed):

*Bud shape.*—Ellipsoid.

*Bud diameter.*—1.3 cm.

*Bud length.*—0.8 cm.

*Bud color.*—RHS 137C with stripes RHS 166A.

Immature flower (at moment of opening):

*Diameter.*—3.0 cm.

*Color upper surface.*—RHS 2D.

*Color lower surface.*—RHS 4D.

Mature flower:

*Diameter.*—9 cm.

*Height.*—2 cm.

*Diameter of disc.*—3 cm.

Ray florets:

*Length.*—3.5 cm.

*Width.*—0.9 cm.

*Shape.*—Oblong.

*Apex.*—Tridentate.

*Base.*—Obtuse.

*Margin.*—Entire.

*Texture (both upper and lower surfaces).*—Smooth, glabrous.

*Number per inflorescence.*—30-38.

*Color, fully opened.*—Upper surface: RHS 155C, lower surface: RHS 155C.

Disc florets:

*Length.*—0.8 cm.

*Width.*—0.1 cm.

*Shape.*—Elliptic.

*Number per inflorescence.*—470.

*Color.*—

*Immature.*—Apex: RHS 7A, Base: RHS 145C.

*Mature.*—Apex: RHS 14A, Base: RHS 145C.

Phyllaries:

*Length.*—0.9 cm.

*Width.*—0.3 cm.

*Shape.*—Elliptic.

*Apex.*—Obtuse.

*Margin.*—Entire.

*Number per inflorescence.*—70.

*Arrangement.*—Imbricate whorls.

*Texture (both upper and lower surfaces).*—Smooth and glabrous with light pubescence present.

*Color.*—Upper surface: RHS 137C with stripes RHS 166A, lower surface: RHS 137D

Peduncle:

*Length.*—4-10 cm..

*Diameter.*—0.3 cm.

*Aspect*.—Upright.
*Texture*.—Light pubescence present.
*Color*.—RHS 137C.

Reproductive organs:

Androecium:

*Presence*.—On disc florets only.
*Number* (*per inflorescence*).—1.
*Filament length*.—0.2 cm.
*Filament color*.—RHS 5A.
*Anthers*.—
*Shape*.—Oblong.
*Anther length*.—0.1 cm.
*Anther color*.—RHS 13A.
*Pollen*.—
*Color*.—RHS 13A.
*Pollen amount* (*generally*).—Moderate.

Gynoecium:

*Presence*.—On disc and ray florets.
*Pistils*.—Number: 1.
*Pistil length*.—0.6 cm.
*Style length*.—0.4 cm.
*Style color*.—RHS 154C.
*Stigma shape*.—Bi-lobed.
*Stigma color*.—RHS 14A.

Seeds: None observed.

Disease resistance: No resistance or susceptibility observed.

Drought tolerance: Not drought tolerant.

What is claimed is:

1. A new and distinct cultivar of *Leucanthemum* plant named 'LEUZ0008', substantially as illustrated and described herein.

* * * * *